United States Patent [19]

Reinehr et al.

[11] Patent Number: 4,579,975

[45] Date of Patent: Apr. 1, 1986

[54] PROCESS FOR PRODUCING STILBENE-4,4′-DIALDEHYDE

[75] Inventors: Dieter Reinehr, Kandern, Fed. Rep. of Germany; Alwyn Spencer, Basel, Switzerland

[73] Assignee: Ciba-Geigy Corporation, Ardsley, N.Y.

[21] Appl. No.: 712,453

[22] Filed: Mar. 13, 1985

Related U.S. Application Data

[63] Continuation of Ser. No. 422,925, Sep. 24, 1982, abandoned.

[51] Int. Cl.$^4$ .................................................. L07C 45/69
[52] U.S. Cl. ........................................................ 568/433
[58] Field of Search ............................ 568/433; 585/436

[56] References Cited

PUBLICATIONS

Journal of Organic Chemistry 43, 2454 (Jun. 9, 1978).
Plevyak et al., Jour. of Org. Chemistry, vol. 43 (1978) 2454–2456.

*Primary Examiner*—Bernard Helfin
*Attorney, Agent, or Firm*—Edward McC. Roberts; Kevin T. Mansfield

[57] ABSTRACT

Stilbene-4,4′-dialdehyde can be produced by reaction of ethylene with 4-bromobenzaldehyde in the presence of a base and of a palladium compound as catalyst in a simple and economical manner in high yields, by performing the reaction under a partial pressure of ethylene of 0.01 to 1 bar. The stilbene-4,4′-dialdehyde obtained is suitable for example for producing optical brighteners.

7 Claims, No Drawings

PROCESS FOR PRODUCING STILBENE-4,4'-DIALDEHYDE

This application is a continuation of application Ser. No. 422,925, filed Sept. 24, 1982, now abandoned.

The invention relates to a novel process for producing stilbene-4,4'-dialdehyde.

Organic compounds substituted by vinyl or allyl groups, inter alia styrene and/or stilbene compounds, can be produced by catalytic reaction of corresponding halides with olefins, for example methyl acrylate or ethylene, in the presence of tertiary amines. Mixtures of palladium acetate and triphenylphosphine or tri-o-tolylphosphine are preferably used as catalysts. The reaction can be performed with or without the addition of organic solvents, such as methanol, acetonitrile, N,N-dimethylformamide, N,N-dimethylacetamide or excess olefin. On reaction of halobenzenes with ethylene under pressure, there are formed, depending on the reaction conditions and/or starting halobenzenes, styrenes and/or stilbenes [cp., for example, U.S. Pat. No. 3,922,299 and J. Org. Chem., 43, 2454 and 43, 2941 (1978)]. According to Bull. Chem., Soc. Japan, 46, 1505 (1973), various olefins, inter alia ethylene or propylene, can be arylated, in the presence of palladium black or $PdCl_2$ and an excess of potassium acetate as acid acceptor, with methanolic solutions of halobenzenes, particularly iodobenzenes. In this prior known process, the palladium compound is used in an amount of at least 1 mol %, relative to the halobenzene.

There has now been found a process for producing stilbene-4,4'-dialdehyde by reaction of ethylene with 4-bromobenzaldehyde in the presence of a base and of a palladium compound as catalyst, in which process the reaction is performed with a partial pressure of ethylene of 0.01 to 1 bar.

By the process according to the invention, stilbene-4,4'-dialdehyde can be produced in a simple, economical manner, under mild reaction conditions, and with the use of readily available 4-bromobenzaldehyde. Under very low partial pressures of ethylene, there is obtained an unexpectedly high yield after surprisingly short reaction times.

The reaction is preferably performed under a partial pressure of ethylene of 0.1 to 1.0 bar. The partial pressures of ethylene as defined can be obtained for example by the introduction of ethylene into the reaction solution under normal pressure, or by the presence of an inert gas in closed reaction vessels.

The types of catalyst and also 4-bromobenzaldehyde are known. Catalysts which are not known can be produced by methods known per se. The ethylene and the 4-bromobenzaldehyde are used in at least a stoichiometric amount.

There can be used as base, in the process according to the invention, compounds of the formula

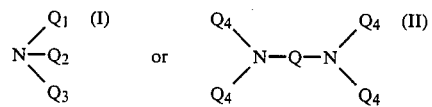

wherein

Q is straight-chain or branched-chain $C_2$–$C_6$-alkylene, $Q_1$ is $C_1$–$C_{12}$-alkyl, cyclopentyl, cyclohexyl or phenyl, or benzyl which can also be substituted, for example by a halogen atom, such as chlorine or bromine, or it is a $C_1$–$C_4$- and especially a $C_1$–$C_2$-alkyl or alkoxy group, $Q_2$ and $Q_3$ are identical or different $C_1$–$C_{12}$-alkyl, and $Q_4$ is methyl or ethyl.

Alkyl groups $Q_1$ to $Q_4$ can be straight-chain or branched-chain. When $Q_1$ to $Q_3$ are alkyl groups, these advantageously together contain at least 9C atoms. Compounds of the formula I are preferably used.

Examples of compounds of the formulae I and II are: triethylamine, tri-n-butylamine, tri-(2-ethylhexylamine), tri-n-octylamine and tri-n-dodecylamine; N-benzyldialkylamines, such as N-benzyldimethylamine, N-benzyldiethylamine, N-(4-chlorobenzyl)-dimethylamine and N-(3-methyl- or 3-methoxybenzyl)-dimethylamine; N,N,N',N'-tetramethyl- and N,N,N',N'-tetraethylethylenediamine, N,N,N',N'-tetramethyl-1,3-diaminopropane and N,N,N',N'-tetramethyl-1,6-diaminohexane. Tri-n-butylamine is preferably used.

The bases are used in at least a stoichiometric amount. There is preferably used an excess of base, for example up to about 5 mols of base, especially 1.25 mols of base, relative to the 4-bromobenzaldehyde.

The reaction temperatures for the reaction according to the invention are advantageously between 30° and 200° C., preferably between 80° and 150° C. The reaction is preferably performed in an organic solvent which is inert to the reactants. Suitable inert organic solvents are cyclic, or N,N-disubstituted, amides, particularly compounds of the formula III $$Q_5Q_6NCOQ_7 \qquad (III)$$

wherein $Q_5$ and $Q_6$ independently of one another are straight-chain or branched-chain $C_1$–$C_8$-alkyl, $C_5$–$C_8$-cycloalkyl or benzyl, or together they are —$(CH_2)_3$—, —$(CH_2)_4$— or —$(CH_2)_2$—O—$(CH_2)_2$—, and $Q_7$ is hydrogen, straight-chain or branched-chain $C_1$–$C_8$-alkyl, or together with $Q_5$ it is —$(CH_2)_q$—, where q is 3, 4 or 5.

Alkyl groups $Q_5$ and $Q_6$ preferably contain 1–5C atoms and especially 1–3C atoms. If $Q_5$ and/or $Q_6$ is (are) cycloalkyl groups, they are in particular cyclopentyl or cyclohexyl. Alkyl groups $Q_3$ preferably have 1 or 2C atoms. The following may be given as examples of compounds of the formula III: N,N-dimethylformamide, N,N-diethylformamide, N,N-di-n-butylformamide, N,N-diisopentylformamide, N,N-dimethylacetamide, N,N-dimethylpropionamide, N-methyl-N-benzylformamide, N-ethyl-N-cyclohexylformamide, N-formylpiperidine, N-formylpyrrolidine, N-acetylmorpholine, N-methylpyrrolidone, N-ethylpyrrolidone and N-methylpiperidone. The solvent which is preferably used is N,N-dimethylformamide, N,N-diethylformamide, N,N-dimethylacetamide or N-methylpyrrolidone. More especially preferred is N,N-dimethylformamide. It is also possible to use N,N,N',N'-tetramethylurea as solvent.

The catalysts used can be for example palladium complexes of the type described in the U.S. Pat. No. 3,922,299, in particular palladium(II) complexes, for example $PdCl_2$, $PdBr_2$, $Pd(CN)_2$, $Pd(NO_3)_2$,

and Pd(OOC-$C_1$-$C_{12}$-alkyl)$_2$, especially palladium acetate, or alternatively palladium(O) complexes, for example complexes of bis-(dibenzylideneacetone)-palladium(O) and bis-(phenylisonitrile)-palladium(O), with trivalent phosphorus or arsenic compounds, such as trialkyl-, triaryl-, trialkoxy- and triphenoxyphosphines or -arsines, or variably substituted trivalent phosphorus or arsenic compounds. Examples of such phosphorus or arsenic compounds are: triphenylarsine, diphenylmethylphosphine, diphenylmethoxyphosphine, trimethylphosphine, triethylphosphine, tri-n-butylphosphine, triphenylphosphine, phenyl-di-n-butoxyphosphine, triphenylphosphite and especially tri-o-tolylphosphine. The complexes mentioned can be used as such, or can be formed in situ, that is to say, in the reaction medium.

The phosphorus or arsenic ligand is advantageously used in a 2-10-fold molar excess, relative to the palladium. Catalysts preferably used are mixtures of $PdCl_2$ or palladium acetate and tri-n-butylphosphine, triphenylphosphine, tri-o-tolylphosphine or triphenylphosphite. Particularly preferred are mixtures of palladium acetate and triphenylphosphine or tri-o-tolylphosphine.

The stilbene-4,4'-dialdehyde obtainable according to the invention can be used to produce known optical brighteners. Optical brighteners of this kind are described for example in the U.S. Pat. No. 4,108,887. The compounds produced according to the invention can also be converted into dyes or optical brighteners in a manner known per se, optionally with the introduction of suitable functional groups, such as amino groups, and/or by sulfonation of the aromatic radicals [cp. for example Encyclopedia of Chemical Technology, 2nd Edition, Vol. 19, pp. 1 to 16]. Stilbene and stilbene derivatives are used also as scintillators, adhesive additives, insecticides or light stabilisers [cp. for example Chemical Abstracts 78, 39352, 84, 137386 and 85, 224416].

The invention is further illustrated by the following Examples without being limited by them.

$$\text{Conversion number} = \frac{\text{mols final product}}{\text{mols Pd compound}}$$

EXAMPLE 1

A stock solution of 0.02244 g (0.0001 mol) of palladium acetate and 0.1216 g (0.0004 mol) of tri-(o-tolyl)-phosphine in 20 ml of dimethylformamide is produced under argon. 9.5 ml of dimethylformamide are placed under ethylene into a reflux apparatus, and 4.63 g (25 mmols) of 4-bromobenzaldehyde, 6.56 mols (22.5 mmols) of tri-n-butylamine and 0.5 ml of stock solution are added. The mixture is stirred, with the simultaneous passing through of ethylene, for 8 hours at 130° C. There are subsequently added to the reaction mixture 20 ml of water, and the stilbene-4,4'-dialdehyde which has precipitated is filtered off. 2.25 g (9.5 mmols) of stilbene-4,4'-dialdehyde are thus obtained, corresponding to a yield of 76% of theory, in the form of yellow crystals, m.p. 170°-172° C. (Pd content 0.01 mol %, relative to 4-bromobenzaldehyde; conversion number 7600, relative to 4-bromobenzaldehyde).

EXAMPLE 2

The procedure is carried out as described in Example 1 but using 4.14 ml (27.5 mmols) of N-benzyldimethylamine instead of tri-n-butylamine. There are obtained 1.77 g (7.5 mmol) of stilbene-4,4'-dialdehyde, corresponding to a yield of 60% of theory (Pd content 0.01 mol %; conversion number 6000).

EXAMPLE 3

The procedure is carried out in the manner described in Example 1 except that N,N-dimethylacetamide is used in place of dimethylformamide. There are obtained 2.37 g (10.0 mmols) of stilbene-4,4'-dialdehyde, which corresponds to a yield of 80% of theory (Pd content 0.01 mol %; conversion number 8000).

EXAMPLE 4

The procedure is carried out in the manner described in Example 1 except that N-methylpyrrolidone is used in place of dimethylformamide. There are obtained 2.22 g (9.4 mmols) of stilbene-4,4'-dialdehyde, corresponding to a yield of 75% of theory (Pd content 0.01 mol %; conversion number 7500).

EXAMPLE 5

The procedure is carried out in the manner described in Example 1 except that N,N,N',N'-tetramethylurea is used instead of dimethylformamide. There are obtained 2.05 g (8.7 mmols) of stilbene-4,4'-dialdehyde, which corresponds to a yield of 69% of theory (Pd content 0.01 mol %; conversion number 6900).

EXAMPLE 6

The procedure is carried out in the manner described in Example 1 except that 0.2 ml of stock solution and 9.8 ml of dimethylformamide are used. After a reaction time of 16 hours, there are obtained 2.33 g (9.9 mmols) of stilbene-4,4'-dialdehyde, corresponding to a yield of 79% of theory (Pd content 0.004 mol %; conversion number 19750).

EXAMPLE 7

The procedure is carried out in the manner described in Example 1 except that 2.5 ml of stock solution and 7.5 ml of dimethylformamide are used. There are obtained 2.22 g (9.4 mmols) of stilbene-4,4'-dialdehyde, corresponding to a yield of 75% of theory (Pd content 0.05 mol %; conversion number 1500).

What is claimed is:

1. A process for producing stilbene-4,4'-dialdehyde by reaction of ethylene with 4-bromobenzaldehyde in the presence of a tertiary amine as base and 0.004 to 0.05 mol %, relative to the 4-bromobenzaldehyde of a palladium (II) or palladium (O)-tertiary phosphine complex as catalyst, which comprises performing the reaction at 80°-150° C. under a partial pressure of ethylene of 0.01 to 1 bar in an inert solvent.

2. A process of claim 1, wherein the reaction is performed in the presence of a mixture of palladium acetate and tri-o-tolylphosphine, as catalyst.

3. A process of claim 2, wherein the reaction is performed under a partial pressure of ethylene of between 0.1 and 1.0 bar.

4. A process of claim 1, wherein the solvent used is a cyclic or N,N-disubstituted amide.

5. A process of claim 1, wherein the base used is a compound of the formula

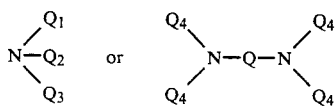

wherein
Q is straight-chain or branched chain $C_2$–$C_6$-alkylene,
$Q_1$ is $C_1$–$C_{12}$-alkyl, cyclopentyl, cyclohexyl or phenyl, or benzyl which can also be substituted, for example by a halogen atom, such as chlorine or bromine, or it is a $C_1$–$C_4$- and especially a $C_1$–$C_2$-alkyl or alkoxy group,
$Q_2$ and $Q_3$ are identical or different $C_1$–$C_{12}$-alkyl, and $Q_4$ is methyl or ethyl.

6. A process of claim 5, wherein the base used is tri-n-butylamine.

7. A process of claim 4, wherein the solvent used is a compound of the formula $$Q_5Q_6NCOQ_7$$

wherein $Q_5$ and $Q_6$ independently of one another are straight-chain or branched-chain $C_1$–$C_8$-alkyl, $C_5$–$C_8$-cycloalkyl or benzyl, or together they are —$(CH_2)_3$—, —$(CH_2)_4$— or —$(CH_2)_2$—O—$(CH_2)_2$—, and $Q_7$ is hydrogen, straight-chain or branched-chain $C_1$–$C_8$-alkyl, or together with $Q_5$ it is —$(CH_2)_q$—, where q is 3, 4 or 5.

* * * * *